United States Patent [19]

Bentley et al.

[11] Patent Number: 4,899,741
[45] Date of Patent: Feb. 13, 1990

[54] LASER HEATED PROBE AND CONTROL SYSTEM

[75] Inventors: Joseph R. Bentley, Holiday; Radford G. Ferre, Midvale, both of Utah; Steven W. Kovalcheck, San Diego, Calif.

[73] Assignee: HGM Medical Laser Systems, Inc., Salt Lake City, Utah

[21] Appl. No.: 180,188

[22] Filed: Apr. 11, 1988

Related U.S. Application Data

[63] Continuation-in-part of Ser. No. 3,209, Jan. 14, 1987, Pat. No. 4,760,209.

[51] Int. Cl.⁴ .............................................. A61B 17/36
[52] U.S. Cl. ...................................... 606/27; 128/398; 374/141
[58] Field of Search ..................... 128/303.1, 395-398, 128/401; 219/121.62, 121.83; 374/141, 142

[56] References Cited

U.S. PATENT DOCUMENTS

| | | | |
|---|---|---|---|
| 3,298,371 | 1/1967 | Lee | 128/303.1 |
| 3,369,549 | 2/1968 | Armao | 128/401 X |
| 3,507,283 | 4/1970 | Thomas, Jr. | 128/303.1 |
| 4,074,719 | 2/1978 | Semm | 128/303.1 |
| 4,476,512 | 10/1984 | Sunago et al. | 361/103 |
| 4,633,872 | 1/1987 | Chafee et al. | 128/303.1 |
| 4,646,737 | 3/1987 | Hussein et al. | 128/303.1 |
| 4,662,368 | 5/1987 | Hussein et al. | 128/303.1 |
| 4,748,979 | 6/1988 | Hershenson | 128/303.1 |
| 4,760,845 | 8/1988 | Kovalcheek | 128/303.1 |
| 4,794,619 | 12/1986 | Tregay | 374/131 |
| 4,796,622 | 3/1987 | Lu et al. | 128/303.1 |

FOREIGN PATENT DOCUMENTS 2826383 12/1979 Fed. Rep. of Germany .
2138297 10/1984 United Kingdom ............. 128/303.1

OTHER PUBLICATIONS

George S. Abela et al., "Hot Tip: Another Method of Laser Vascular Recanalization", Surgery and Medicine 5:327-335 (1951).

Robert L. Protrell et al., "The Heater Probe: A New Endoscopic Method for Stopping Massive Gastrointestinal Bleeding", Gastroenterology 74, 257-262 (1978).

Primary Examiner—Lee S. Cohen
Attorney, Agent, or Firm—Olive & Olive

[57] ABSTRACT

A laser-energizable thermal probe apparatus useful for laser angioplasty procedures comprises a heat generating probe assembly connected to the distal end of an optical fiber, the proximal end of the fiber being connected to a source of laser energy. A thermocouple mounts on the probe assembly and is connected to control the temperature of the probe assembly in use.

18 Claims, 8 Drawing Sheets

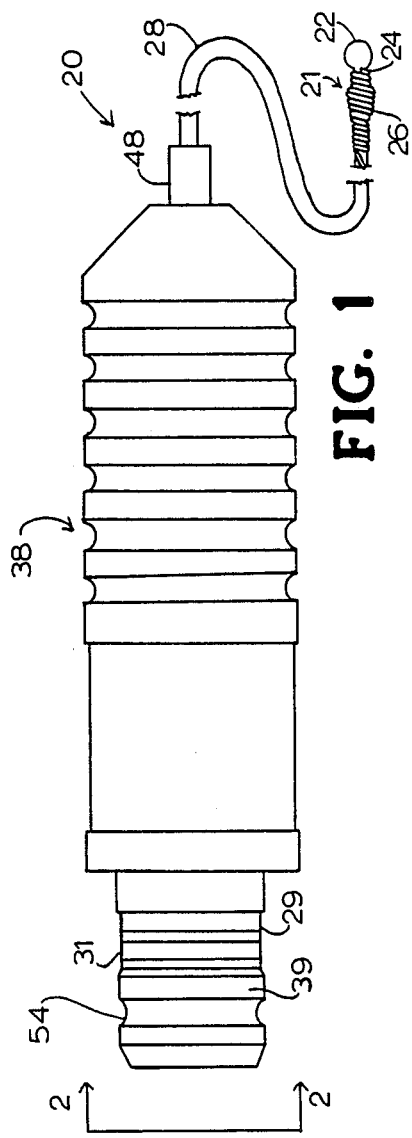
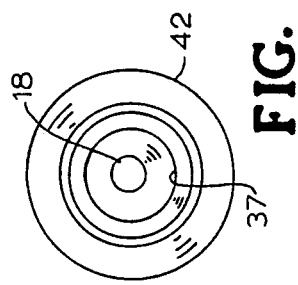
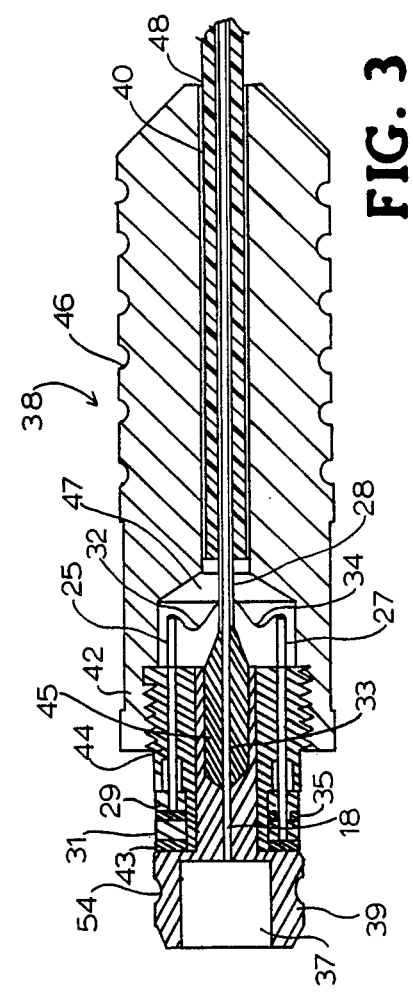

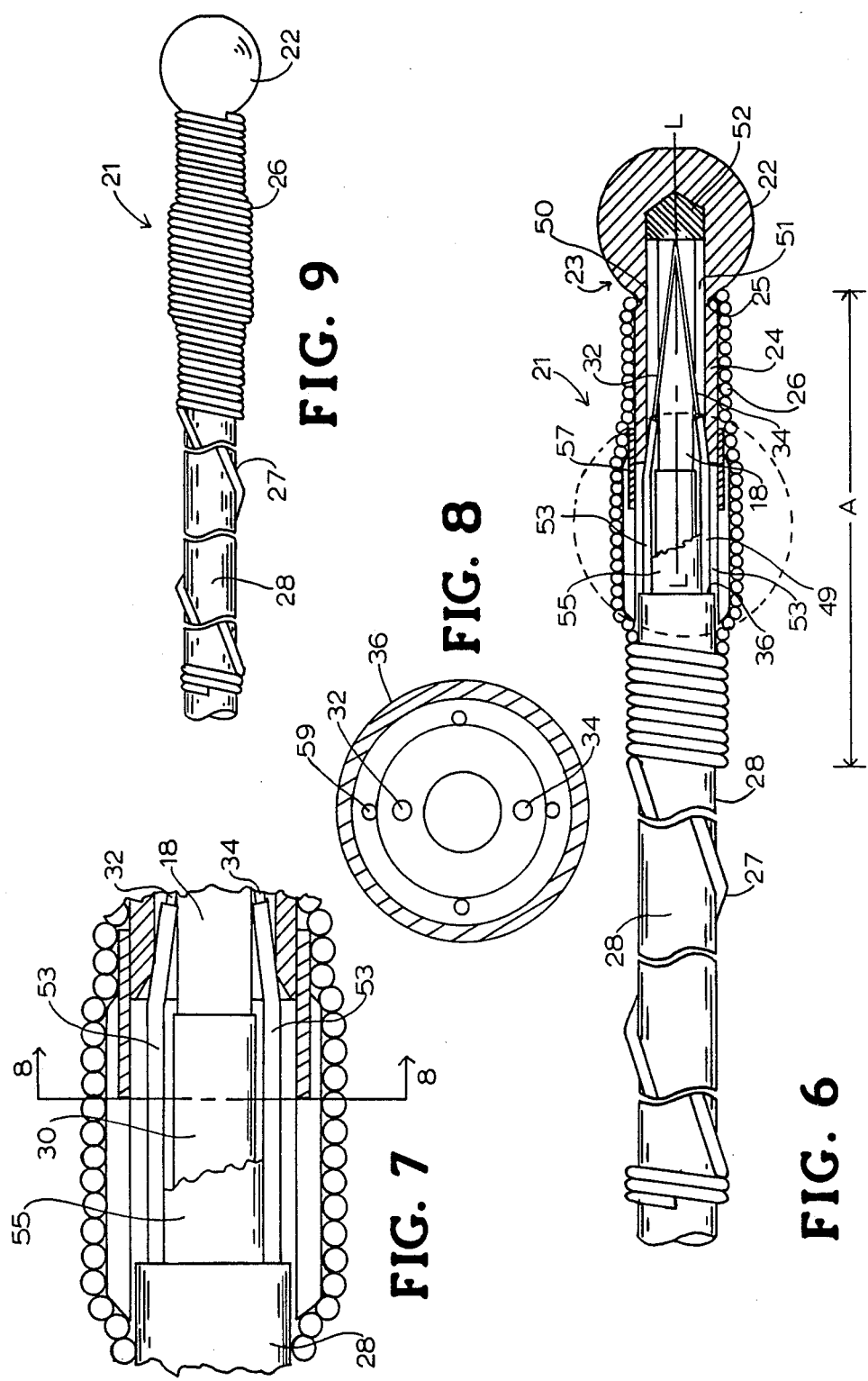

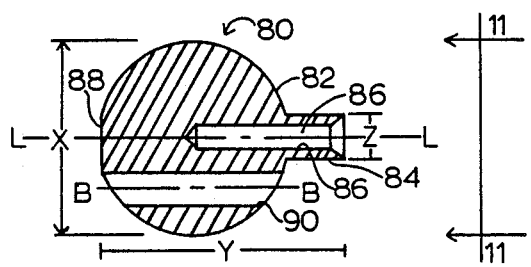
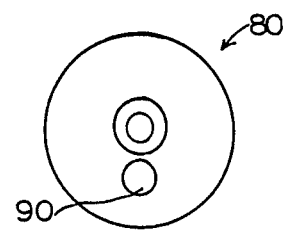
FIG. 10   FIG. 11
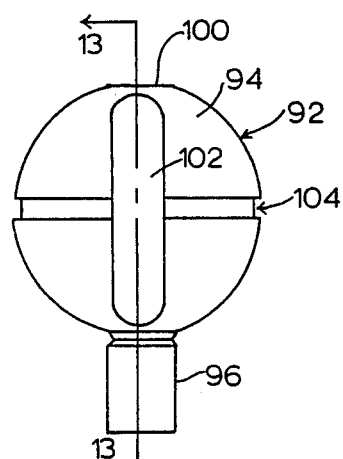
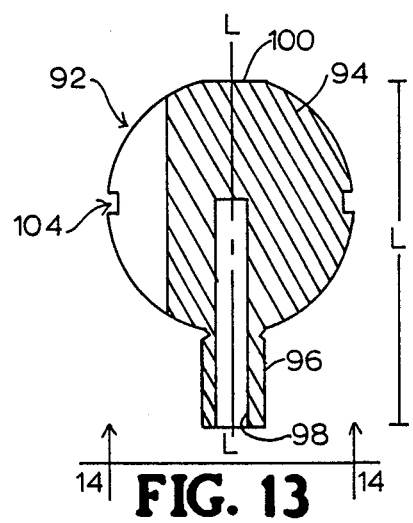
FIG. 12   FIG. 13
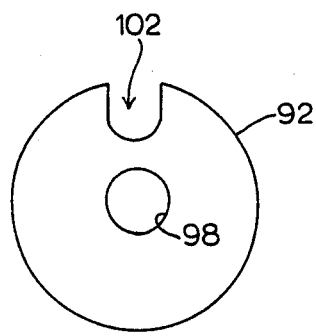
FIG. 14

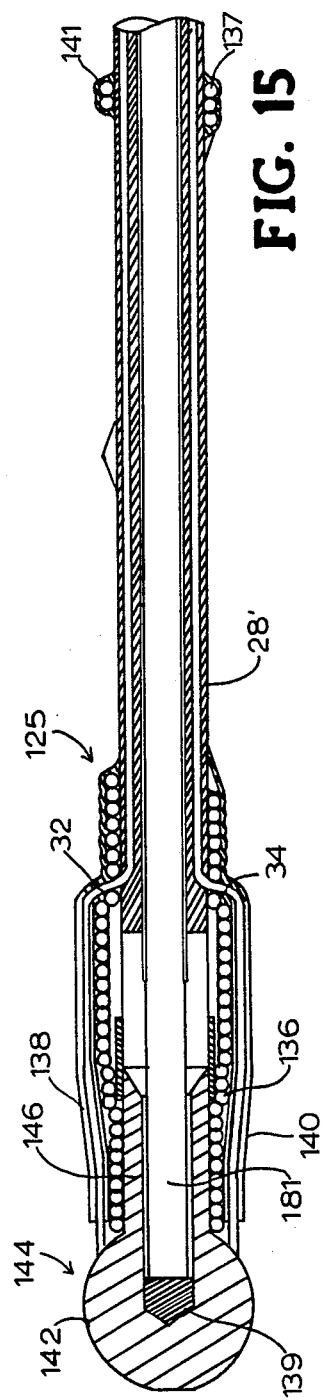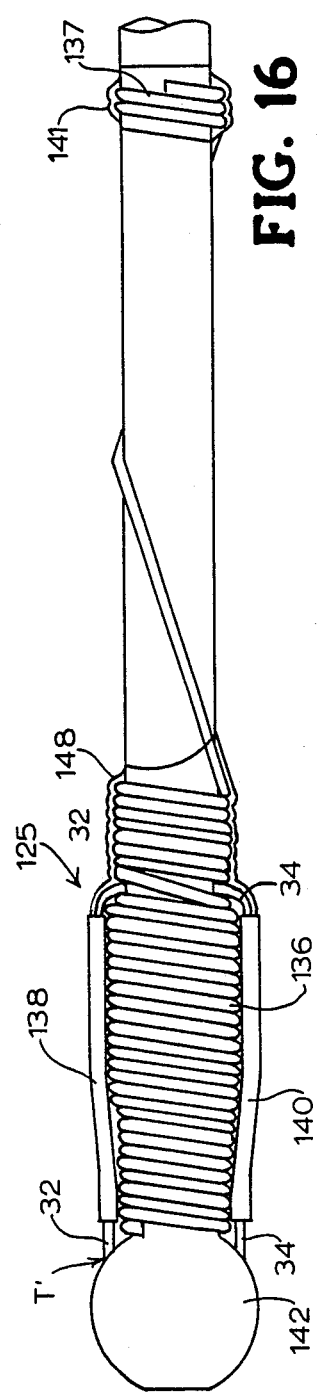

LASER HEATED PROBE AND CONTROL SYSTEM

RELATED APPLICATION

This application forms a continuation in part of application Ser. No. 003,209, filed Jan. 14, 1987 entitled "Laser Angioplasty Probe", now U.S. Pat. No. 4,760,209.

BACKGROUND OF THE INVENTION

1. Field of the Invention

The invention relates to an improved laser light heated probe and to a system and its components for controlling the temperature of a probe mounted at the distal end of an optical fiber to which laser light is transmitted to heat the probe. The invention has special application in angioplasty procedures wherein tissue is heated for the recanualization of occluded blood vessels by removal of intravascular plaque and thrombi therefrom. Other applications include the occlusion of unwanted blood vessels such as varicose veins and the heat treating or glazing of the internal lumen of blood vessels.

2. Description of the Related Art

An extensive review of related prior art is given in the related patent application Ser. No. 003,209. Such review is incorporated herein by reference but is summarized and supplemented here as necessary for background to the present invention. Since the immediate and primary application of the invention is directed to angioplasty procedures, the related art will be explained primarily in connection with that type of application recognizing however that the invention has even broader application than that described.

A medical laser system of a type useful in practicing the present invention is to be found in U.S. Pat. No. 4,633,872. Aspects of the present invention concern an improved temperature sensing and laser power control system for a laser heated probe and which may be used as a modification of the type of laser system described in the patent.

As referred to in the prior application, occlusive heart disease, involving blockage of important coronary arteries, is a major cause of death among persons in the adult population. Even where death does not occur as a result of such disease, occluded arteries in the extremities, liver, kidney, and brain nonetheless may lead to severe discomfort, loss of normal activity, and altering of the individual's quality of life.

The treatment of patients with occlusive arterial disease has generally been affected by two primary methods: pharmacological treatment for moderate arterial obstructions, and surgical treatments, including arterial bypass surgery and/or percutaneous transluminal angioplasty(PTA), in instances of severe stenosis. The benefits of PTA, as contrasted to bypass surgery, include less traumatic procedures, lower costs, respectable success in opening arterial occlusions, and relatively short patient recovery times. A primary disadvantage of PTA, however, is that the material causing the arterial blockage, e.g. arterial plaque or thrombi, is not removed but only pushed aside, with the possibility of future occlusions resulting from the continued accretion of plaque and/or thrombi to the displaced occluding deposits.

Laser irradiation has been proposed for the permanent removal of the aforementioned material deposits. The methods of laser irradiation which have been proposed include: (1) direct laser irradiation, in which intravascular plaque and thrombi are removed through abalation, and (2) indirect laser irradiation in which laser energy is converted to thermal energy through the interaction of a laser beam with an absorptive thermally conductive device, which when brought into close proximity or contact with plaque or thrombic complexes, dissolves, melts or evaporates the artery-blocking material.

The present invention insofar as it applies to laser angioplasty procedures is basically directed to the indirect laser irradiation technique and involves the insertion of an optical fiber into the arterial or venous channel, to function as a transmissive element for delivery of laser energy to a thermally conductive device for use at the treatment site. Cooling and temperature control of the probe are of critical concern and constitute the primary concerns of the invention.

Another concern of the invention is that of avoiding the introduction into the patient's body, particularly at the treatment site, of any type of electrical device which might create an electrical or magnetic perturbation capable of damaging or interferring with electrocardial functions. Another concern of the invention is ensuring that the thermally conductive device of the invention is suitably attached to the optical fiber such that it will not become disengaged during use. The invention is thus directed to dealing with each of these concerns in a manner not satisfactorily dealt with before by prior art indirect laser irradiation apparatus.

Federal Republic of Germany Pat. No. 2,826,383 published Dec. 20, 1979 is cited along with other references in U.S. Pat. Nos. 4,646,737 and 4,662,368. The earlier German patent as well as the two later U.S. patents disclose a heat generating element in the form of a metal probe mounted on an optical fiber through which light is transmitted to generate heat energy in the heat generating element. The German patent refers to cooling by flowing a gas within a casing to a location near the treatment site to extract heat from the heat generating element but does not disclose means for controlling the temperature of the heat generating element. The German patent mentions but does not describe or illustrate use of a thermocouple in a sheath tube surrounding the optical fiber. U.S. Pat. No. 4,646,737 also refers to use of a cooling fluid directed alongside the optical fiber as a means for cooling the heat generating element. U.S. Pat. No. 4,662,368 also refers to use of a cooling gas to cool the heat generating element.

U.S. Pat. Nos. 4,646,737 and 4,662,368 discuss a means for monitoring probe temperature by monitoring reflected infrared radiation emanating from a laser light heated probe during laser deactivation. Such a method does not lend itself to real time monitoring or control of probe temperature since the laser is turned off during the measurement or measurements made during the cooling cycle of the probe. In practice, probes as depicted in U.S. Pat. Nos. 4,646,737 and 4,662,368 have relied heavily on a dosimetry matrix for estimation of probe temperature in which prior in-vitro data was accumulated which relates probe temperature to input laser power level. Such a dosimetry matrix is highly variable and dependent upon the fluid dynamic environment surrounding the probe body. As a result, large deviations from predicted probe temperatures are possible. For reference see U.S. Pat. No. 4,662,368 and an article by George S. Abela et al entitled "Hot Tip:

Another Method of Laser Vascular Recanalization" published in Surgery and Medicine 5:327-335, 1985.

The laser energized thermal probe described in prior application Ser. No. 003,209 teaches use of a coiled thermally conductive wire as a means of joining the probe body to the optical fiber and providing a substantially improved means for preventing the probe from becoming disengaged during use. This helically wound heat conductive wire also serves as a means for dissipating heat generated by the probe in use thus avoiding the need for cooling fluids and the like. In another aspect of the laser energized thermal probe of the prior application, there is provided a mass of a laser energy-absorptive, thermally conductive, high emissivity medium contained within the interior of the probe tip which functions to maximize the absorption of the laser energy by the probe.

What the present invention seeks to achieve is a still further improved laser heated probe by incorporating with the probe apparatus invention of the prior application, means for real time sensing and controlling the temperature of the heat generating element and controlling the laser power to maintain some predetermined temperature. Since the present invention is directed to providing a unique thermocouple controlled temperature sensing and temperature and power control system for an optical fiber mounted probe, mention is made of U.S. Pat. No. 4,476,512 in which a relatively low temperature measuring heat-sensitive element is positioned at the output end of an optical fiber as a means of sensing abnormal changes in the surface temperature of the fiber at its output end and thereby interrupting the laser power delivery should abnormal changes in optical fiber temperature be detected. The optical fiber and relative low temperature measuring heat-sensitive element lead are shown as separate elements. This patent also illustrates and discusses the prior art practice of using a measure of light entering the fiber for power control. The system of this patent is apparently directed to the direct laser irradiation technique since it makes no disclosure of using the light energy to heat a probe or the like. Furthermore, precise control of optical fiber surface temperature by varying input laser power is not addressed nor is the measurement of relatively high temperature of a probe heated by laser energy as with the present invention.

Electrically heated probes for vascular treatment are known. The article "The Heater Probe: A New Endoscopic Method For Stopping Massive Gastrointestinal Bleeding" by Robert L. Protell et. al. Gastroenterology 74, pages 257-262(1978), for example, describes an electrically heated, hollow, cylindrical metal probe which can be passed via an endoscope to apply pressure and heat simultaneously to a bleeding vessel. The electrically heated probe comprises a hollow aluminum cylinder with an inner heater coil wound on a ceramic core. A thermocouple element contained within the heater coil within the probe tip measures the actual temperature and feeds this information back to a servo-mechanism which maintains a selected temperature at the desired level. Such a probe inherently requires the presence of electrical current proximate the operative site, is large with respect to arterial and venous vessel diameters and is also characterized by having a relatively slow response time with respect to heating and cooling of the probe. Such a probe also has the disadvantage of being limited in the temperature to which the tip can be raised because of the wire size, power supply and like considerations.

What can be observed from the foregoing description is that the advent of the laser heated probe has provided a means for insuring permanent removal of blood vessel-occluding material. The laser heated probe disclosed in prior patent application Ser. No. 003,209 also illustrates that the blood vessel occluding material can be removed without requiring introduction of an external supplied coolant medium to the treatment site and without requiring the presence of an electrical current or electrical heater at the site.

Accordingly, it is an object of the present invention as with the invention of the prior application Ser. No. 003,209 to provide a laser heated probe operating at a relatively high temperature which is efficiently cooled through conductive means, does not require the introduction of an externally supplied coolant medium to the treatment site and provides a probe having a high degree of structural integrity.

A more specific object is to provide a thermocouple equipped laser heated probe forming part of an improved temperature sensing and laser power control system for applying the indirect laser irradiation technique particularly as it applies to laser angioplasty. The advantage of relatively simple calibration and of being able to readily monitor the sensing outputs for all temperatures likely to be encountered are thus other objects of the present invention as achieved through coupling the laser heated probe with the laser power control system via a temperature sensing thermocouple hereafter described.

Other objects and advantages will be more fully apparent from the ensuing disclosure and appended claims.

SUMMARY OF THE INVENTION

The present invention provides a temperature and laser power monitoring system for use in an indirect laser irradiation procedure in which laser energy is converted to thermal energy through the interaction of a laser beam with an absorptive, thermally conductive device, i.e. a probe, capable of being brought into close proximity or contact with plaque or thrombic complexes to dissolve, melt or evaporate the artery-blocking material. The invention further provides such a system in which a relatively high temperature sensing thermocouple is incorporated in a laser heated probe mounted on an optical fiber with the thermocouple leads being incorporated in the casing assembly and element which carries the optical fiber and also being connected to the control system. The invention also provides a system in which the laser energy heated probe has its excess heat dissipated without requiring flow of a coolant medium to the probe.

The invention permits monitoring of the probe temperature and laser power with the thermocouple being incorporated as part of the probe so as to both sense and measure the amount of heat generated by the light passed through the optical fiber.

The thermocouple control circuitry of the invention effectively couples the probe temperature sensor to the laser light feedback circuit thereby supporting real time control of the laser output power necessary to maintain desired preset probe temperature. The invention control system uniquely adapts to controlling laser heated probes of different size and mass without user intervention and thus is a "smart" control.

A unique male/female connector arrangement for coupling the optical fiber to the laser source and the thermocouple leads to the control circuitry is described. The present description will be best understood by making reference to the previously mentioned U.S. Pat. No. 4,633,872 as illustrating an overall medical laser control system for which the present invention provides an improved modification particularly useful in laser angioplasty procedures.

Other aspects and features of the invention will be more apparent from the ensuing disclosure and appended claims.

BRIEF DESCRIPTION OF THE DRAWINGS

FIG. 1 is an elevation view of a laser angioplasty treating assembly according to the invention and disassociated from its laser power source.

FIG. 2 is an end view of the plug body forming part of the FIG. 1 assembly and taken in the direction of line 2—2 of FIG. 1.

FIG. 3 is a sectioned elevation view of the plug assembly forming part of the FIG. 1 assembly for coupling the laser angioplasty treating assembly of FIG. 1 to a laser power source and associated control circuitry.

FIG. 6 is a partially-sectioned elevation view of the probe assembly portion of the laser treating assembly shown in FIG. 1, illustrating the details thereof according to the first embodiment.

FIG. 7 is an enlarged partially-sectioned view of the portion of the probe assembly of FIG. 6 enclosed in the dashed circular line seen in FIG. 6.

FIG. 8 is a section view taken along line 8—8 of FIG. 7 illustrating placement of the spines.

FIG. 9 is an elevation view of the probe assembly shown in FIG. 1.

FIG. 10 is a sectional elevation view of a probe assembly body disclosed in prior application Ser. No. 003,209 featuring a guide wire passage radially spaced from, and parallel to, the central axis of the body and useful with the various embodiments of the present invention incorporating a thermocouple with the probe assembly.

FIG. 11 is an end elevation view of the probe body of FIG. 10 taken in the direction of line 11—11 of FIG. 10.

FIG. 12 is a top plan view of a probe body of another embodiment disclosed in prior application Ser. No. 003,20 and useful with the various embodiments of the present invention which incorporate a thermocouple with the probe assembly.

FIG. 13 is a sectional view of the FIG. 12 probe body, taken along line 13—13 of FIG. 12.

FIG. 14 is an end elevation view of the probe body of FIG. 12 taken in the direction of line 14—14 of FIG. 13.

FIG. 15 is a partially-sectioned elevation view of the probe assembly portion of the laser treating assembly shown in FIG. 1 illustrating in a second embodiment the details of another arrangement of the thermocouple element.

FIG. 16 is an elevation view of the probe assembly shown in FIG. 15.

DETAILED DESCRIPTION OF THE INVENTION, AND PREFERRED EMBODIMENTS THEREOF

Figure 4:
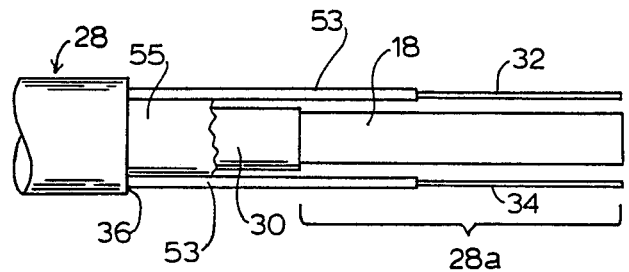
FIG. 4 is an elevation view of the distal end of the element encasing the optical fiber and thermocouple leads as they appear prior to formation of the thermocouple by electrically connecting the two thermocouple wires at their distal ends according to a first embodiment.

Although the laser-energized device of the prior invention set forth in patent application Ser. No. 003,209 as well as the present invention are described as a "laser angioplasty probe," having specific utility for recannalization of occluded blood vessels, it will be apparent that the utility of the present as well as the prior invention is not thus limited, but extends to any suitable heating operation in which the device may be usefully employed, including, but not limited to, heating, cauterizing, and removing tissue, etc.

In tissue-heating applications, the laser-energized probe of the present invention as with the prior invention allows for safe, effective, and efficient delivery to a tissue site of thermal energy, by transmission and conversion into heat of laser energy. However, unlike the prior invention, the present invention incorporates a uniquely arranged temperature sensor placed within, attached to or otherwise fixed proximate the probe and provides temperature sensing which is subsequently used for temperature control at the site.

The probe assembly which is connected to the optical fiber in the device of the present invention as with the prior invention comprises a thermally conductive probe body having a curvoidal tip at its distal portion. As used in such context, the term "curvoidal" refers to any three-dimensional shape having a predominantly convex, curved surface. The curvoidal tip may thus, for example, be of a shape selected from those of the group consisting of spherical, spheroidal, and ellipsoidal shapes, e.g., and oblate spheroidal shape. Of the foregoing shapes, spherical tips are generally preferred in practice.

The spherical shape provides substantially uniform thickness in the treating area, provides optimum multi-directional heat transfer, provides minimum resistance to flow around the sphere and within the vessel, is least likely to perforate and follows the path of least resistance in the vessel.

The probe assembly of the present invention as with the probe assembly of the prior application Ser. No. 003,209 comprises a thermally conductive probe body and a helically wound heat conductive wire as a joining means to secure the probe body to the optical fiber. The thermocouple sensor of the present invention is incorporated into the assembly. The probe body comprises a curvoidal tip, and a neck portion joined to the tip and extending proximally therefrom. An interior passage in the probe receives the distal end of the fiber in proximity to, and preferably within, the tip, whereby laser energy transmitted by the optical fiber to the probe body and converted to thermal energy is transmittable from the probe tip to a selected site in contact therewith.

The determination of real time temperature of the curvoidal tip surface of the probe is of prime concern since it is the heated surface of the tip which will come into close proximity or contact with vascular tissues. Two embodiments are presented which detail the attachment of the temperature sensing element to the curvoidal tip. In addition to its material and thermal properties, the rate of heating of the curvoidal tip by absorption of laser light is related to the mass and volume of the curvoidal tip, whereas the rate of cooling or heat loss of the tip is related to its mass and surface area. To an extent, the ratio of tip surface area to tip volume determines the placement of the temperature sensing element for efficient surface temperature determination. Empirical data shows that when the curvoidal tip of the invention is placed in a fluid field, a tip with a diameter greater than 2 millimeters may develop a substantial temperature gradient between the internal passage in the tip and its external surface. Empirical data also indicates that the temperature gradient occurring in heated tips with diameters equal to or less than 2 millimeters is in practice inconsequential. Accordingly, two embodiments are presented for placement of the temperature sensing element in order to adequately and efficiently monitor tip surface temperature. In all embodiments the temperature sensing element is effectively shielded from the laser light.

In a first embodiment involving curvoidal tips with diameters of 2 millimeters or less, temperature sensing leads are bonded at their distal ends to form a strong electrical contact and thermocouple. The thermocouple is positioned internally within the curvoidal tips interior passage. The interior passage and cavities in the probe body to the extent not filled by the optical fiber and affixed thermocouple and thermocouple leads are filled with a high temperature, chemically stable, thermally conducting, thermally shock resistant, electrically insulating compound to substantially eliminate any cavity and thereby substantially eliminate pressure build up and gas accumulation within the probe. Boron nitride is particularly suited to this purpose though ceramic adhesives are applicable and may be applied in liquid form and allowed to set. For the present invention as with prior application No. 003,209, a helically wound thermally conductive wire is joined at the distal portion of the probe neck and at the proximal portion of the casing surrounding the optical fiber and provides the probe to optical fiber structural connection and an extended heat transfer dissipation path for heat generated by the probe assembly when in use.

In the first embodiment involving tips with diameters of 2 millimeters or less, the thermocouple is secured to the surface of the distal end of the optical fiber within the mentioned interior passage. The thermocouple effectively measures the relatively high temperature of the probe and effectively ignores the effect of any relatively low temperature rise in the optical fiber cladding. In this first embodiment, the thermocouple leads are enclosed by the helically wound heat conductive wire which extends from the neck portion of the curvoidal tip to the casing surrounding the optical fiber.

In a second embodiment for tips of greater diameter than 2 millimeters, the temperature sensing or thermocouple leads emerge from the helically wrapped wire connector between adjacent coils at the distal end of the casing surrounding the optical fiber. The thermocouple leads at their respective distal ends are welded to the probe tip which effectively acts as an electrical conductor to electrically connect or bridge the distal ends of the thermocouple leads forming the thermocouple. Alternatively, the two thermocouple leads of the second embodiment can be bonded together at their distal ends to form an electrical connection and thermocouple and this bonded joint may in turned be bonded, preferably welded, to the probe tip. According to the "Law of Intermediate Metals," (see Robert P. Benedict: *Fundamentals of Temperature, Pressure and Flow Measurements,* John Wiley & Sons Inc., New York, 1969) when a third metal (in this case material of the curvoidal tip) is inserted between two dissimilar metals of a thermocouple junction such third metal will have no effect upon the output voltage of the thermocouple as long as the two junctions formed by the additional metal are at the same temperature. Thus, both of the described methods of attachment of the thermocouple to the external surface of the curvoidal tip are essentially equivalent. This equivalence has been confirmed by empirical methods.

The interior passage and cavities in the second embodiment probe body to the extent not filled by the optical fiber are, as with the probe assembly of the first embodiment, filled with a high temperature, chemically stable, thermally conductive, thermal shock resistant, electrically insulating compound to substantially eliminate gas accumulation within the probe. Boron nitride is particularly suited to this purpose though certain ceramic adhesives are applicable as previously stated in reference to the first embodiment. It is readily evident from what has been described that the external placement of the thermocouple on curvoidal tips with diameters of 2 millimeters or less is an optional third embodiment. In this latter third embodiment as with the second embodiment the thermocouple leads are affixed to the exterior of the helically wound heat conductive wire from which they are electrically insulated.

In another aspect of the laser-heated thermal probe described above, a mass of a laser energy-absorptive, thermally conductive, high emissivity medium, is interiorly contained in a central portion of the curvoidal tip in proximity to and preferably in intimate contact with, the distal end of the optical fiber. For tip diameters of 2 millimeters or less, the thermocouple of the invention may be fixed adjacent the distal end of the optical fiber immediately adjacent the high emissivity medium.

In still another aspect of the invention, the helically wound heat conductive wire is welded at its distal portion to the probe body, and adhesively bonded at its proximal portion to a casing or jacket surrounding the optical fiber. In a further aspect, such helically wound heat conductive wire may have successive turns thereof spot welded to one another, for enhanced mechanical integrity of the wire coil, preferably with finite spacings between the successive turns to permit pressure relief incident to heating of the probe assembly and associated portions of the optical fiber in use. In this aspect of the invention, the thermocouple leads are independently coated with a durable, flexible, biocompatible, electrically insulating material, preferably a flouroplastic. The coated thermocouple leads are in turn encased within the casing or jacket of the optical fiber.

The element housing the optical fiber is fabricated so as to contain the leads from the thermocouple and which are in turn coupled to the temperature control circuitry. The temperature is both sensed and controlled. Means are provided for displaying the temperature and detecting errors and faults. The thermocouple leads are illustrated as extending parallel to the optical fiber in a common casing or jacket. However, it is contemplated that the thermocouple leads could be wound on the optical fiber in a double helix form without crossing.

It is appreciated that the placement of the thermocouple leads within the optical fiber casing will alter the direction of flexure and the flexibility of the optical fiber cable. It has been found that when the cross sectional diameter of the thermocouple leads are 1/5th of the cross sectional diameter of the optical fiber core/clad, no practical difference in flexure direction nor flexibility was evident between configurations whereby the thermocouple leads are positioned parallel to or loosely coiled about the optical fiber core/clad assembly. However, it has also been found that helical placement of the thermocouple leads about the optical fiber core/clad assembly is preferable to prevent directional dependent flexure of the optical fiber cable particularly when the cross sectional diameter of the thermocouple leads is greater than 1/5th of the cross sectional diameter of the optical fiber core/clad. The thermocouple leads, when placed within the optical fiber casing or jacket are separated from the optical fiber core/clad by 0.01 to 0.05 millimeter layer of compliant casing or jacket material. This thin layer of casing or jacket material acts as a buffer to dissipate the transfer of stress between the thermocouple leads and the optical fiber core/clad during the extrusion of the outer optical fiber casing or jacket or during the bending or axial stressing of the optical fiber cable.

Referring now to the drawings, FIG. 1 sows an elevation view of a laser treating assembly 20 comprising a laser-heated probe, optical fiber cable, power and thermocouple coupling assembly according to a first embodiment of the invention. In this first embodiment construction, the probe assembly 21, comprising a thermally conductive probe body including a spherical tip 22 and a cylindrical neck 24, and a helically wound thermally conductive wire 26, is disposed at the distal portion of a specially constructed composite optical fiber and thermocouple lead element 28, with the proximal end of said element being disposed in plug connector 38 as described hereinafter in greater detail.

Element 28 (FIGS. 4 and 5) includes an optical fiber 18 e.g., a quartz fiber having a bend radius of about 2 centimeters and a diameter of about 100–600 microns, fixed within a composite cladding 30 providing both a mechanical support and protective barier for the otherwise brittle and easily damaged fiber. The composite structure of optical fiber 18 and cladding 30, is designated as a "dressed optical fiber".

A pair of negative and positive thermocouple leads 32,34 extend along cladding 30 and within an outer protective jacket 36. Leads 32, 34 (FIG. 4) are independently coated with a durable, flexible, biocompatible and electrically insulating coating 53 and are separated from the optical fiber cladding by a thin layer of the optical fiber casing or jacket material 55 preferably with a thickness of 0.01 to 0.05 millimeter. Leads 32, 34 in this first embodiment are joined at their distal ends to form a thermocouple T secured by adhesive to the distal end of optical fiber 18. While thermocouple leads 32, 34 are illustrated as extending both generally straight and parallel to each other the invention contemplates that the leads 32, 34 could be wound about element 55 in a double helix, non-crossing array when found necessary for signal enhancement or bendability in the more critical applications. In a later described second embodiment of the thermocouple configuration illustrated in FIGS. 15 and 16 the thermocouple leads 32, 34 are mounted external of the probe assembly 28 rather than within the probe assembly as in FIG. 6.

An illustrative dressed optical fiber 18 which has been found useful as a component of element 28 in the practice of the present invention comprises (i) a 200 micron diameter high-purity quartz optical fiber core, (ii) a 240 micron diameter doped quartz clad layer providing a numerical aperture of 0.24 thereon and (iii) a 260 micron diameter buffer layer formed of HardClad non-optical polymer, manufactured by Ensign-Bickford Industries, Inc., Simsbury, Conn. The quartz clad layer (ii) and polymer buffer layer (iii) form the previously referred to composite cladding 30. The composite cladding 30, is covered with the thin jacket 55 comprising, in one example, clear Tefzel 210 material manufactured by E. I. duPont de Nemours & Co. Inc., Wilmington, Del. and which serves to separate the thermocouple leads 32, 34 from the composite cladding 30. A 550 micron outer jacket formed of black Tefzel 210 material, manufactured by E. I. duPont de Nemours & Co., Inc., Wilmington, Del. serves as the final casing 36. In this construction, the high density plastic buffer layer (iii) serves as a support medium uniformly contacting the doped quartz clad layer (ii) and permitting bending of the fiber, while the outer jacket protects the buffer layer and enhances the flexibility of the fiber. The thin layer of jacket material 55, serves to dissipate the transfer of stresses between the thermocouple leads and the optical fiber core/clad which might develop during fabrication of the optical fiber cable or during bending or axial stressing of the optical fiber cable. The jacket 36 comprises a black flouroplastic material useful in preventing the escape of nuisance laser light.

Each of the diameter values set forth above for the successive outer layers of the dressed fiber refers to outer diameter of the designated layer together with the associated core and any layer(s) interior to the designated layer. Of course, many other sizes, types and configurations of optical fibers may be used in the broad practice of the present invention without departing from the scope and substance thereof.

Fluoroplastic insulated thermocouple leads 32, 34 extend outside the composite cladding 30 but within the protective jacket 36 to complete element 28. Positive and negative leads 32, 34 made of a chromel and alumel composition respectively were 0.05 millimeter in diameter in the example previously referred to. With fluoroplastic insulation, the nominal diameter of the thermocouple leads was 0.076 millimeters in the same example.

Element 28 including the optical fiber 18 and thermocouple leads 32, 34 in the vicinity of their proximal ends are disposed in a plug like male connector 38. Plug connector 38 (FIGS. 1 & 3) provides means for optically connecting the laser power source to the optical fiber 18 and for electrically connecting the thermocouple leads 32, 34 to the later described temperature sensing and control circuitry.

Connector 38 is internally threaded at its proximal portion 42 to mate with a correspondingly externally threaded plug body 44. It will be appreciated that parts 42 and 44 in FIG. 3 may be connected by means other than threading. An external ridged portion 46 provides for manual gripping. Connector 38 provides a male fitting configured to be slidably engageable with a corresponding female fitting 150 described in reference to FIG. 17 forming part of a laser apparatus to effect the desired optical and electrical coupling. An annular groove 54 receives a position sensing switch, not shown, forming part of the optical delivery system to indicate to the control panel when the probe is in use.

It will of course be appreciated that connector 38 may be formed as a female fitting with the laser being provided with an appropriate corresponding male fitting. It will likewise be appreciated that other configurations of the coupling assembly may be employed to secure the optical fiber in proper alignment with a source of laser radiation emitted from a laser source, whereby laser energy is focused into the fiber.

Figure 17:
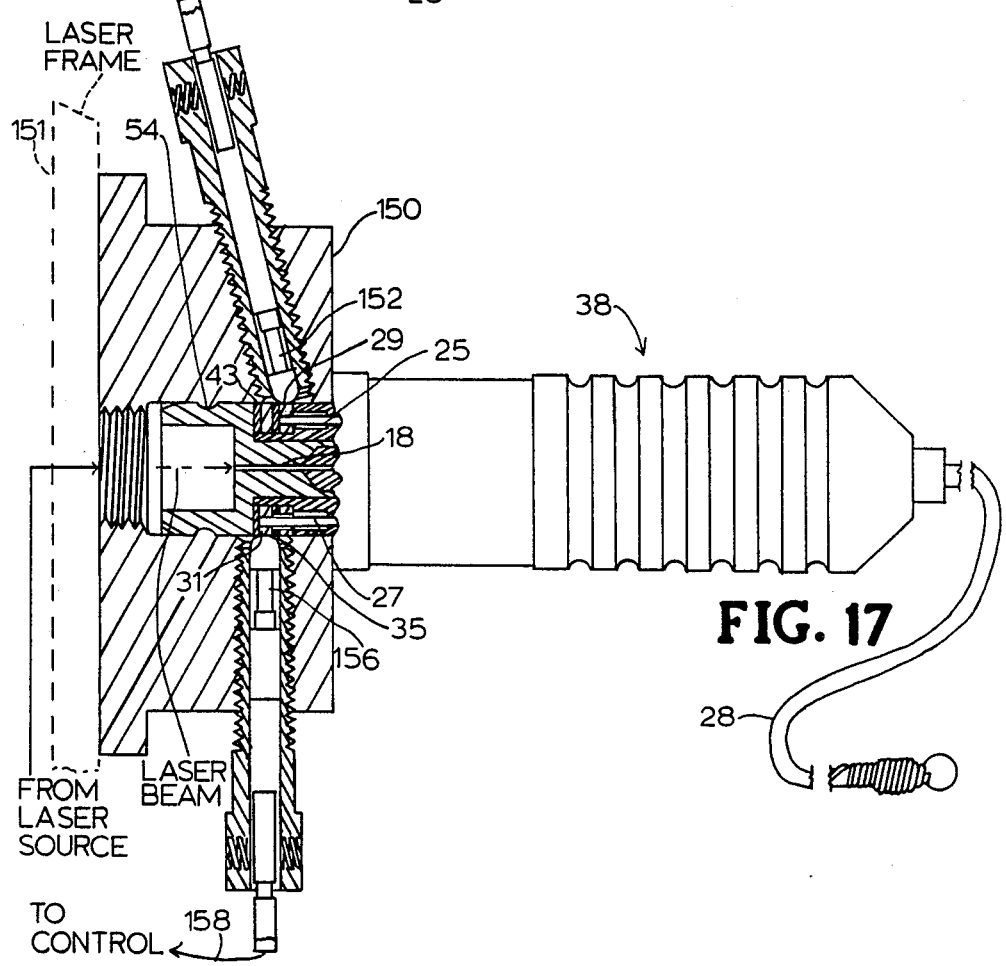
FIG. 17 is a partially sectioned view of the plug assembly of FIG. 3 and its mating female receptacle with interlock switches which indicate when the plug is fully engaged and centering pins which provide optical alignment being eliminated for simplicity of illustration.

Electrical connections are made to the thermocouple leads 32 and 34 through pins 25 and 27. Pin 25 connects to annular conductive ring 29 and pin 27 connects to annular conductive ring 31. Pin 27 passes through but is electrically insulated from ring 29. Rings 29 and 31 provide means for connecting leads 32 and 34 to the laser control as seen in FIG. 17 and with reference to the laser temperature and power control circuitry, later described. The proximal ends of leads 32 and 34 are bonded to pins 25 and 27 respectively to form an electrical contact. The preferred method of bonding is welding though soldering of leads 32 and 34 to pins 25 and 27 is acceptable. An electrically insulating spacer 35 separates rings 29 and 31 and another electrically insulating spacer 43 separates ring 31 from plug member 39.

Connector 38 includes a cylindrical cavity 37 in which the optical fiber 18 terminates. Cavity 37 is provided so that if the laser beam is misaligned with the optical fiber 18 when connector 38 is installed as in FIG. 17, and strikes the surface of cavity 37, the laser beam will be confined within connector 38. Further, the positioning of the proximal portion of the fiber 18 within the cavity 37 insures that the proximal end of the fiber 18 will not be damaged during storage or handling. Fiber 18 is secured within plug member 39 by means of a suitable adhesive 33. Additional support of the proximal end of the optical fiber 18 is provided by potting the optical fiber 18 into the plug member 39 using a suitable potting material 45 such as a silicone adhesive.

The optical fiber and thermocouple lead element 28 is sheathed over the initial portion of its length extending distally from connector 38 in a covering 48 of a urethane, vinyl, rubber, or other suitable material, such sheath extending through central cavity 40 of connector 38, in the manner shown. Covering 48 serves to provide strain relief protection for the optical fiber and thermocouple lead cable assembly 28 and connector 38 connection.

The optical fiber 18 is dressed as previously described along the major portion of its length and in the passage 40 on connector 38 and is undressed at its proximal portion in the cavity 47 of the rigid portion 46 as well as in the vicinity of the probe assembly, as next described.

Figure 5:
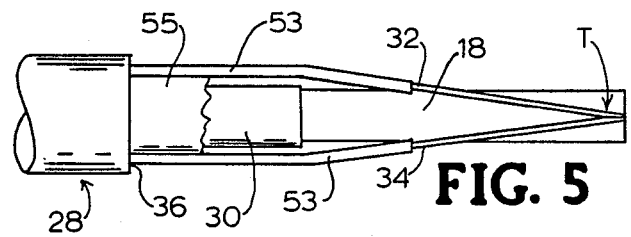
FIG. 5 is an elevation view similar to FIG. 4 illustrating the distal ends of the thermocouple lead wires joined together and secured to a distal end of the optical fiber to form a thermocouple at such distal end according to the first embodiment.

Enlarged FIG. 4 illustrates the distal portion 28a of the optical fiber-thermocouple element 28 in which such distal portion 28a represents a portion from which the cladding 30 and buffer layers 55 and 36 have been removed from the optical fiber 18 and from which the electrical insulation 53 has been partially removed from the thermocouple leads 32 and 34. FIG. 5 illustrates the FIG. 4 construction after the pair of thermocouple leads have been joined by welding or other means to form a thermocouple T. A suitable ceramic or other adhesive, not shown, is applied to the undressed portions of optical fiber 18 and to the electrically uninsulated end portions of the thermocouple leads 32 and 34 which acts both to adhere and electrically insulate the leads 32 and 34 on the undressed optical fiber 18. A coating of boron nitride followed by curing has been found suitable for the purpose. Assuming that the proximal end of the optical fiber-thermocouple element 28 has already been installed in the connector 38 as previously explained the thermocouple equipped distal end of element 28 is now ready to be installed in the probe assembly 21. The description next turns to describing the probe assembly 21 and how the element 28 is joined to the probe assembly 21 to complete the overall laser treating assembly 20 seen in FIG. 1.

FIG. 6 shows a detailed partially sectioned elevation view of the probe assembly 21 of the FIG. 1 embodiment of the invention, together with an associated portion of the optical fiber-thermocouple lead element 28. Probe assembly 21 comprises a probe body 23 having a spherical tip 22 and cylindrical neck 24. For purposes of the present invention, probe body 23 is formed as described in copending application Ser. No. 003,209 of a suitable heat-conductive material, preferably a metal, with suitable illustrative metal materials including platinum, iridium and platinum/iridium alloys. Of the foregoing illustrative metals, platinum/iridium alloys are the most preferred materials of construction.

The probe body 23 comprising the spherical tip 22 and cylindrical neck 24 may be integrally formed, by any suitable method, such as casting, molding, machining, etc. It is also within the purview of the present invention as in copending application Ser. No. 003,209 to provide a probe body of separately formed constituent tip and neck elements which are bonded or otherwise secured to one another, providing that the method of joining results in suitable mechanical integrity under use conditions. Nonetheless, as previously alluded to, the overall probe assembly 21 is subjected to tensile and compressive forces in use, and to ensure the structural integrity of the probe assembly 21 under such stress conditions, it is generally preferred in practice to provide the probe body as an integrally formed article.

As shown in FIG. 6, the probe body 23 is formed with a central interior passage 50 extending through the neck portion 24 and into the spherical tip 22. The passage is preferably coaxial with the central axis L—L of the probe body 23, to centrally accommodate the undressed optical fiber 18 in passage 50 so that uniform radial heat transfer is effected.

To continue the description of the probe assembly 21, the mentioned thermocouple T once installed in passage 50 resides adjacent a mass of laser energy-absorptive, thermally conductive, high emissivity material 52 installed in passage 50 in the interior of the tip 22, as shown. As used herein, the term "high emissivity" means an emissivity of at least 0.80 (the emissivity of an ideal "black body" being taken as 1.0), consistent with high absorptivity and low reflectance of the laser energy impinged on the material. Preferably, the emissivity of the material is in the vicinity of 1.0. A preferred material for the high emissivity mass 52 is nuclear grade compressed graphite, although any other suitable high emissivity, high absorptivity, low reflectance material, responsive to laser energy to convert the same into thermal energy for transmission to the tip 22, may be employed, e.g., carbon black, platinum oxide powder, etc.

The high emissivity mass or core 52 is disposed within the tip 22, preferably centrally therein and in abutting relation to the polished face of the distal light emitting end of optical fiber 18 and immediately adjacent thermocouple T. Laser energy transmitted by the optical fiber 18 thus impinges on the heat conductive mass 52 and is converted to thermal energy which in turn is transmitted via conduction and radiation to the tip 22. Tissue or other material placed in contact with the external surface of tip 22 is consequently subjected to rapid and intense heating.

It will be appreciated that in some instances, probe body 23 may be constructed without the high emissivity core 52 if probe body 23 is constructed of a suitable laser energy-absorptive material of low reflectance providing a sufficient rate of conversion of laser energy to thermal energy for the desired end use. Nonetheless, the use of a high emissivity core in tip 22 is generally preferred in practice as it provides a highly efficient laser energy to thermal energy conversion medium.

As previously discussed in connection with both the prior invention of copending application Ser. No. 003,209 and the present invention, a particular requirement of the probe assembly 21 for employment in end use environments in which the probe assembly 21 is subjected to significant tensile and compressive stresses, is the provision of a high-integrity joining means for connecting the probe body to the optical fiber. It will be particularly appreciated that in angioplasty applications, the separation of the probe body from the optical fiber is a serious event generally requiring immediate surgical intervention, and entailing potentially catastrophic occurrences if such separation is not immediately detected and corrected. It is also recognized that heat dissipation is a significant consideration and such joining means should also desirably facilitate cooling portions of the probe assembly to dissipate excess heat in areas of the probe assembly not required for treatment.

Accordingly, it is a specific feature of the present invention to provide a thermocouple equipped probe assembly 21 with a helically wound thermally conductive wire 26 as a stress resistant joining means for coupling the probe body 23 to the optical fiber-thermocouple lead element 28 and also for use as a heat dissipation device. The helically coiled wire 26 may be joined at its distal portion by spot welding to the neck portion 24 of the probe body 23. The juncture of the tip 22 and neck 24 portions of the probe body 23 may include a circumferentially-extending groove 25, and the first turn of the coiled wire 26 may be disposed and spot welded or otherwise joined to the tip and/or neck portions of the probe body in the vicinity of this groove 25 as in FIG. 6. The helically wound wire coil 26 may also, as previously mentioned, be spot welded or otherwise permanently joined to the probe body 23 along the length of the neck 24 contacted by the wire 26 forming the coil, as necessary or desirable for the specific end use application. The wire wrapping on neck 24 is enhanced by welding a platinum/iridium ribbon, 57 (FIG. 6) on neck 24 on which are welded a plurality of circumferentially spaced spines 59 (FIG. 8). Spines 59 are used to facilitate welding adjacent wire coils.

To increase the mechanical integrity of the helically wound conductive wire coil 26, successive turns thereof may be spot-welded to one another. While such welding of the turns in the coil does reduce the effective thermal conduction path provided by coil 26, the heat dissipation benefits of the wire coils are so great in magnitude that even with turn-to-turn welding and coil to spine welding, the thermal conduction heat dissipation path provided by coil 26 is still substantially longer than that of a tubular heat dissipation structure.

Welding of adjacent turns in the coil is preferred, since it allows for finite spacing between weld points, where no turn-to-turn coil attachment exists. Such finite spacing between weld points provides openings in the coil structure which allow relief of pressure, such as may arise in operation due to heating and expansion of air or other gas trapped in any void within the proximal portion of probe assembly 21.

As an alternative to welding, any other suitable method or means of bonding or rigidly joining the coiled wire 26 to the probe body 23 may be employed. Nonetheless, where the probe body is constructed of a metal material it is preferred to employ welding as the joining method to maximize coil to coil bonding strength. The space 51 and the cavity 49 in FIG. 6 to the extent not filled with the distal end of the optical fiber 18 and the thermocouple leads 32, 34 are filled with a temperature resistant, chemically stable, thermally conductive, thermally shock resistant, electrically insulating compound to substantially eliminate pressure build up and gas accumulation within the probe. Boron nitride is particularly suited to this purpose as well as appropriate ceramic adhesives.

At its proximal end, the wire coil 26 may feature one or more turns 26 having an angular orientation, relative to the centerline of the probe assembly, greater than that of the other turns in the structure as shown for example for coil strand 27 in FIG. 6. While illustrated as a single helical wrap 27 the invention contemplates that wrap 27 could, for example, be a dual non overlapping helical wrap when desired for additional axial strength. The proximal portion of the coil assembly 26 is affixed to the optical fiber-thermocouple element 28, by adhesive bonding of the coil 26 to the outer casing 36 of the thermocouple-optical fiber element 28, or by any other suitable means or method of securing the proximal portion of the coil 26 to the element 28. The proximal portion of the coil 26 may, for example, be adhesively bonded to the outer casing 36 of element 28, using a suitable high temperature-resistant adhesive bonding medium with preferred materials having good thermal resistance at temperatures on the order of 100° C. and higher. The adhesive bonding medium may be any material meeting the applicable thermal stability and compatibility criteria for the intended end use environment. It is also desirable that a biocompatible epoxy coating cover the exposed surfaces of coil 26. Preferred materials for angioplasty applications include biocompatible epoxies satisfying the criteria for PHS Class 6 materials, such as EE0079/HD0070 epoxy, commercially available from Hysol Division of The Dexter Corporation, Pittsburg, Calif., and EPO-TEK Type 301 epoxy, commercially available from Epoxy Technology, Inc., Billerica, Mass.

The helically wound thermally conductive wire 26 provides an extended heat transfer dissipation path for heat generated in the heat conductive tip 22 and neck 24 of the probe body 23 when in use. The probe body 23 formed of a heat conductive material thus in addition to transmitting heat to tissue in proximity therewith, conducts heat to the helically wound thermally conductive wire 26 so that heat is transmitted and dissipated along the successive turns of the coil in a proximal direction relative to the tip 22 of the probe body 23. In this manner, a highly extended heat dissipation surface area is provided, relative to the axial length of the coil.

To accommodate such heat transfer dissipation function, the helically wound coil 26 is constructed of a thermally conductive material, which may be the same or different from the material of construction of the probe body comprising tip 22 and neck 24. In practice, for the example previously referred to, the preferred material for coil 26 is a platinum/iridium alloy with a cross sectional diameter of 0.076 millimeters.

In general, the number of turns of the helically wound conductive wire 26 in the coil is dependent on the length of wire 26 required to allow the high temperature generated at the tip 22 of the probe body to be diminished to a level equal to or below the recommended operating temperature of the fiber's jacket and buffer layers, in order that the optical fiber 18 and probe assembly 21 are not damaged in use. This is critical where elevated temperatures, e.g., as high as 450° C., are employed.

In such high temperature applications, the heat generated must be dissipated quickly and efficiently in order to avoid the aforementioned damage. This is readily accommodated by the helically wound coil 26 in the probe assembly 21 of the invention.

As an example, for a given temperature, e.g., 450° C., the helical wrapping of a conductive wire having a diameter equal to the wall thickness of a tubular heat-dissipative structure with an equivalent heat-dissipating capacity, provides the same temperature drop as the tubular structure over a substantially reduced axial distance. For example, in the probe assembly design shown in FIG. 6, the required axial length A of a helically wound wire coil providing the same thermal dissipation path (conduction only) is approximately 1/25 of the length of the corresponding tubular structure.

It is to be noted that the construction shown in FIG. 6 provides an annular space 49 between the helically wound wire coil 26 and the buffer layer-coated optical fiber 18. Another annular space 51 surrounds optical fiber 18 and thermocouple leads 32, 34 within cavity 50. To minimize gas accumulation, annular spaces 49 and 51 are filled with a high temperature filler such as boron nitride or a silicone oxide ceramic filler. The filler selected should have at least the characteristics of being fluid when applied, resistant to high temperature and thermal shock, an electrical insulator and thermally conductive. All of which are ideally exhibited by boron nitride.

FIG. 10 shows a probe body 80 useful with the thermocouple equipped probe assembly 21 of the invention. Probe body 80 comprises a generally spherical tip 82 and a cylindrical neck 84 integral therewith. As previously discussed, the probe body may be molded, cast, machined or otherwise produced from a metal such as platinum/iridium alloy. The tip may, for example, have a cross-sectional diameter, i.e., a diametral dimension, perpendicular to the longitudinal centerline L—L of the probe body 80, on the order of 2.5 millimeters, while the axial length Y of the probe body, as measured along the axial center line L—L, may, as a further example, be on the order of 3.2 millimeters. The diameter Z of the neck portion (outer diameter) may be on the order of 0.62 millimeters for the first embodiment and 0.53 millimeters for the second embodiment. The interior diameter of passage 86, accommodating the insertion of the distal portion of the optical fiber 18, may be on the order of about 0.38 millimeters for the first embodiment and 0.28 millimeters for the second embodiment. The larger dimensions for the first embodiment allow for the insertion of both the optical fiber and the thermocouple leads whereas the smaller dimensions of the second embodiment allow for the insertion of the optical fiber only.

In general, the neck portion 84 of the probe body is desirably constructed with a minimum diameter and length consistent with secure assembly to the optical fiber-thermocouple element 28, and preferably with an outer diameter approximately the same as the diameter of the outer casing 36 of element 28 (see e.g., FIG. 6). The internal channel 86 extends preferably from the outer end of the neck 84 to the center of the spherical tip 82 and has a diameter which allows for a sliding fit with the undressed optical fiber 18. As in the other probe body embodiments previously described, the central passage 86 provides a receptacle for mating with the distal end of the optical fiber 18, and accommodates at its innermost portion a mass of high emissivity material, which may suitably be of a type as previously described in connection with the FIG. 6 embodiment of the invention.

The tip 82 of the probe body shown in FIG. 10 is substantially spherical in shape and may have a small localized planar distal face 88 resulting from the machining operation by which the probe body is formed. A guide passage 90 is provided, which is parallel to the central axis L—L of the probe, but radially displaced therefrom. This feature is more clearly shown in FIG. 11, which is a proximal end elevation view of the probe body as shown in FIG. 10. The guide passage 90 accommodates a guide wire (not shown) which is inserted therethrough and defines a travel path along which the probe assembly may be directionally guided in use.

In an embodiment of the FIGS. 10-11 device having utility for angioplasty applications, the diameter of the guide passage 90 may, for example, be on the order of 0.44 millimeters, with the central axis B—B of this passage being at a radial distance of 0.64 millimeters from the central axis L—L of the probe body.

FIGS. 12-14 show an alternative configuration for the probe body. FIG. 12 is a top plan view of such alternative probe body 92. FIG. 14 is a proximal end elevation view of such probe body 92, and FIG. 14 is a sectional view thereof taken along line 13—13 of FIG. 12. Probe body 92 comprises a substantially spherical tip 94 integrally formed with a cylindrical neck 96, wherein the cross-sectional diameter of the tip 94 may be on the order of 2.0 millimeters, and the outer diameter of the neck portion 96 on the order of about 0.53 millimeters. The probe tip 94 may have small frontal planar face 100 as previously described.

As shown in FIG. 13, the probe body 92 includes a central axial passage 98, with a diameter which may, for example, be on the order of 0.28 millimeters, and with a length L, as measured along axial centerline L—L, of about 1.83 millimeters. As in the other probe bodies previously described, the central passage provides a receptacle for mating with the distal end of the optical fiber 18, and for receiving a mass of high emissivity material, which may suitably be of a type as previously described in connection with the FIG. 6 embodiment of the invention.

As shown in FIGS. 12 and 13, tip 94 of the probe body 92 includes a concave recess 102, having a radius of curvature at the trough thereof, which is on the order of about 0.2 mm. The purpose of recess 102 is to accommodate a guide wire, the dimensions of the probe body 92 being sufficiently small that an interior guide wire passage, as used in the probe body of FIGS. 10 and 11, cannot be employed.

Running circumferentially around the tip 94 in a direction generally perpendicular to the longitudinal axis L—L of the probe body 92, is a concave recess 104, the purpose of which is to accommodate a wire wrapping, not shown, which overlies and thereby retains the guide wire in position in recess 102. Thus, a guide wire of 0.014 inch diameter may be retained in recess 102 by three overlying turns of 0.003 inch diameter platinum-/iridium wire in recess 104, with each of the turns being welded to the tip at several discrete points.

The probe body embodiments shown in FIGS. 10-14 may usefully be employed in thermocouple equipped probe assemblies connectable to laser energy supply means in the manner generally described in connection with the probe assembly embodiment of FIG. 1.

It will be appreciated that the dimensions of the various embodiments illustratively set forth hereinabove are for the purpose of facilitating understanding of the invention, and that other dimensions and dimensional relationships may be employed within the broad scope of the invention. In general, the cross-sectional diameter of the probe body's tip may range from about 1 to about 4 millimeters.

Where the diameter of the tip is at the lower end of the aforementioned broad range, e.g., on the order of 1.5 to 2 millimeters in diameter, the construction of the general type shown in FIGS. 12-14 herein may be usefully employed. In this dimensional range, the probe body is highly guideable in character so that it does not require the use of guide wires, as normally employed with arterial probes.

Where the diameter of the tip is at the upper end of the aforementioned broad range, i.e., on the order of 2.5 to 4 millimeters in diameter, the construction of the general type shown and described in connection with FIGS. 10 and 11 herein may be usefully employed with the thermocouple control of the invention, in which the tip is constructed with a passage accommodating a guide wire for directional guidance of the probe assembly along a predetermined travel path.

Making reference next to FIGS. 15 and 16 there is shown the second embodiment of the probe assembly 125 characterized by having the thermocouple leads 32 and 34 enclosed within an electrically insulating tubing 138 and 140 with the distal ends of the thermocouple leads 32 and 34 being welded directly to the tip 142 of the probe body 144 which includes a neck portion 146. Coil 136 serves the same function as the previously described coil 26 (FIG. 6) and is bonded to the optical fiber casing by an epoxy adhesive and includes wraps 137 covered by an epoxy coating 141. Probe body 144 includes a highly heat conductive mass 139 against which the distal end of the optical fiber 181 abuts. Coil 136 is joined to the optical fiber-thermocouple lead element 28' and to the neck portion 146 in the manner previously described. It will thus be appreciated that the primary difference between the probe assembly embodiment previously described and the probe assembly embodiment illustrated in FIGS. 15 and 16 is with regard to mounting thermocouple leads 32 and 34 directly on the probe tip 142 thus establishing the thermocouple with an electrical circuit completed by probe tip 142. For effective and efficient control of the laser heated probe temperature, the second embodiment is the assembly configuration of choice for probe tip diameters of 2.5 millimeters or greater. In other respects, the probe assembly 125 is made and operates in the manner previously described.

Having now described the various embodiments of the probe assemblies associated with the present invention the description next makes reference to FIGS. 17-20. Such description is next directed to describing in reference to FIG. 17 the manner in which the probe assembly is coupled to the laser source and control circuitry and in reference to FIGS. 18-20 the unique circuitry aspects of the present invention relating to power and temperature control as compared to the control circuitry of U.S. Pat. No. 4,633,872 illustrating and describing an overall medical laser system of the type to which the present invention is readily adapted and upon which the present invention seeks to improve.

Making reference initially to FIG. 17 there is illustrated a mounting block or female receiver assembly 150 which mounts on a laser frame 151 in the manner of FIG. 1 of U.S. Pat. No. 4,633,872. Various interlocks for indicating when plug 38 is properly seated as well as the plug locating pin for insuring optical alignment have been eliminated for the purpose of simplifying the FIG. 17 illustration.

What is to be understood in reference to the present invention is that the previously described male plug connector 38 to which the optical fiber-thermocouple lead element 28 and probe assembly 21 are secured as in FIG. 1 is received by the mounting assembly or female receptacle 150, attached to the laser frame 151 by means not illustrated. The previously described pin 25 (FIG. 3) connected to annular conducting ring 29 makes electrical contact with the spring loaded pin 152 connected to electrical lead 154 which connects to the later-described control circuitry. In a similar manner the previously described pin 27 connected to the thermocouple lead 34 is also connected to annular conducting ring 31 (FIG. 3). Ring 31 makes contact with the spring loaded pin 156 which in turn connects to the outgoing thermocouple lead 158 connected to the control circuitry. When plug connector 38 is properly seated in receiver 150, it will be seen that continuous communication between the probe tip and laser control is established. It will thus be understood how the thermocouple signal created by the thermocouple T (FIG. 5) or thermocouple T' (FIG. 16) is connected to the control circuitry and how the light beam from the laser source is directed into the optical fiber 18. The description next turns to a more detailed description of those aspects of the thermocouple control circuitry illustrated in FIGS. 18-20 forming part of the present invention.

Figure 18:
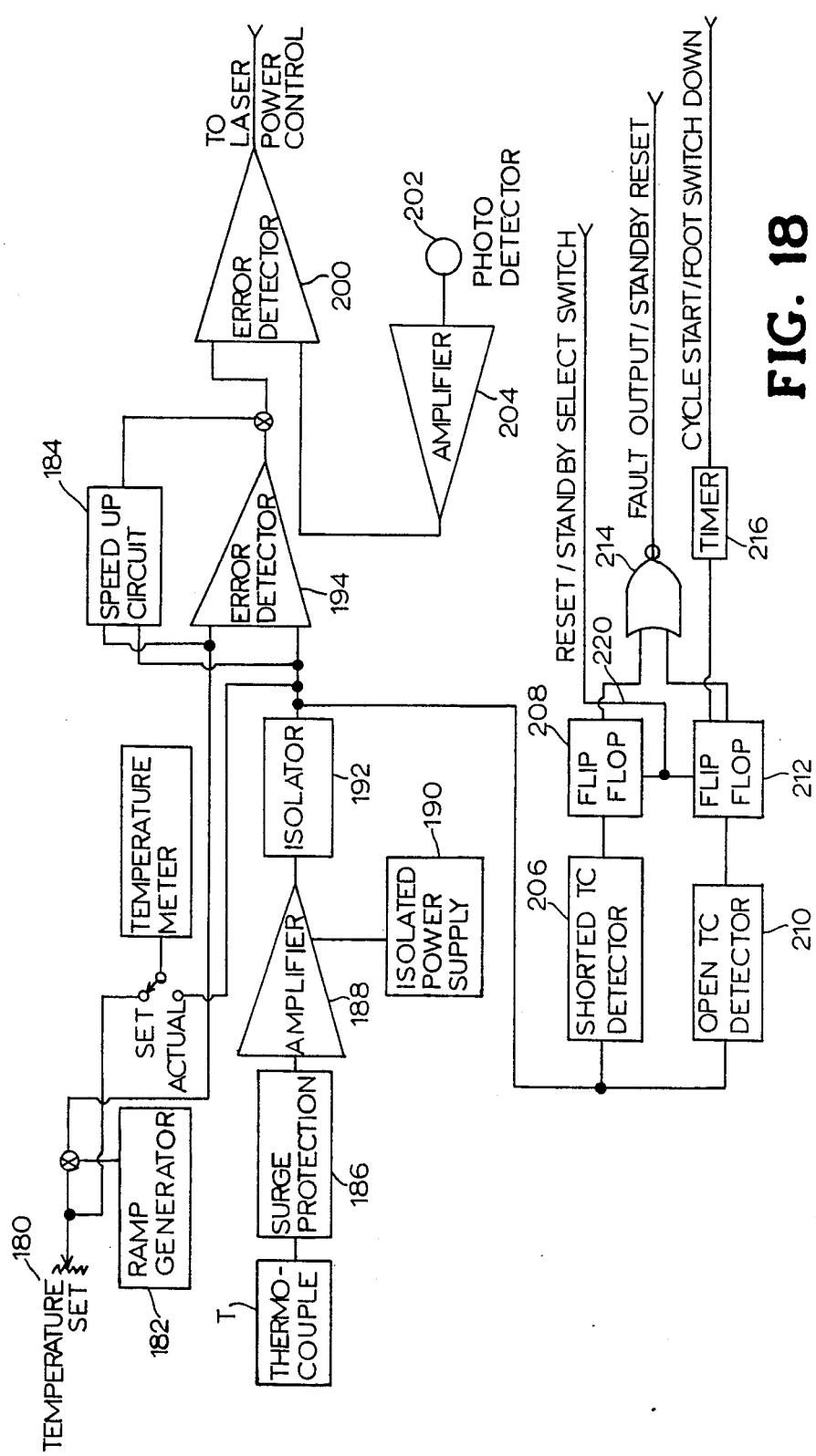
FIG. 18 is a generalized block diagram illustrating components of the control system of the present invention useful with and as a modification of the type laser system described in U.S. Pat. No. 4,633,872.
Figure 19:
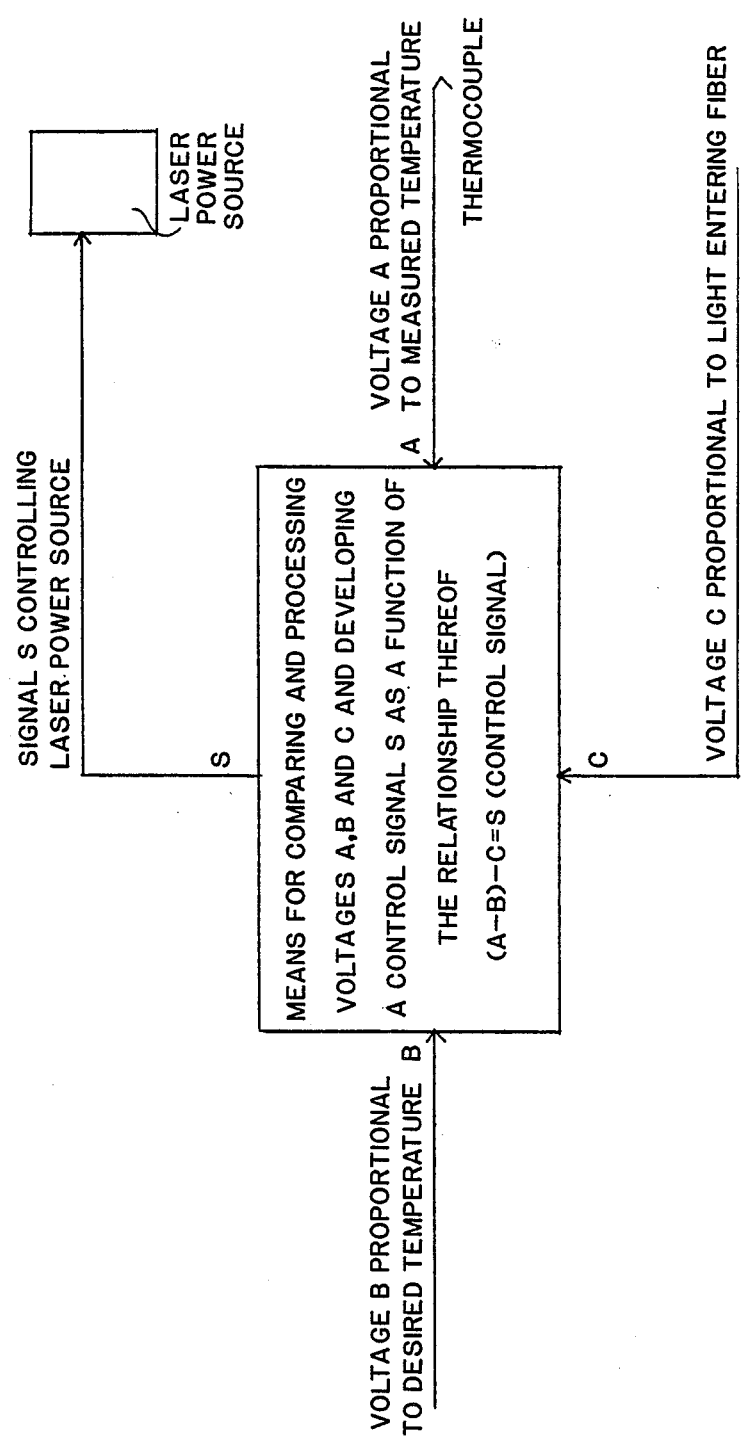
FIG. 19 is a generalized block diagram of a portion of the control system of FIG. 18 for processing three selected voltage signals to obtain a desired laser power control signal.
Figure 20:
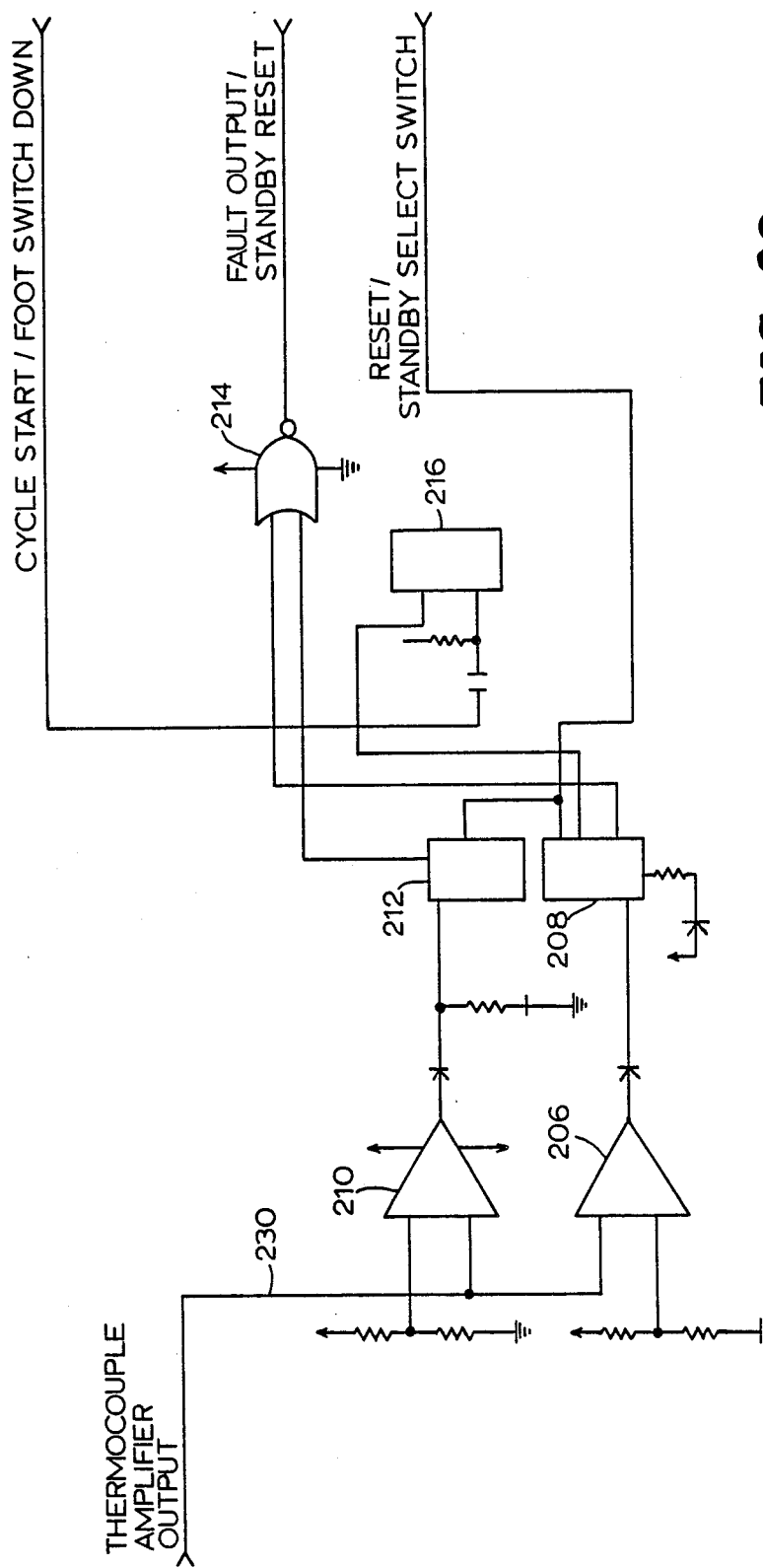
FIG. 20 is a more detailed circuit diagram for the short and open detection circuitry portion of FIG. 18.

Reference is again made to U.S. Pat. No. 4,633,872 for a more complete description of the type of overall system in which the present invention may be applied. FIGS. 18-20 of the present application are thus primarily directed to those circuitry features of the present invention which modify or supplement the circuitry of the '872 patent to facilitate use of the unique thermocouple controlled probe assembly of the invention particularly in an angioplasty procedure. FIGS. 18–20 also illustrate how certain of the '872 circuitry elements are incorporated into the circuitry of the present invention to provide the thermocouple sensing and power control of the invention. FIGS. 18–20 also illustrate how the sensed thermocouple voltage is used to indicate real time absolute temperature, to measure the change of temperature and to establish a closed loop system in which the probe temperature is maintained at a desired preset level appropriate to the angioplasty or other procedure being performed.

At the outset it should be understood that the plug receiver 150 illustrated in FIG. 17 is typically mounted on the front panel of the laser as is the probe receiver of the '872 patent. Therefore in use, the operator or physician initially installs the connector 38 into the receiver 150 on the laser panel following which the operator powers up the laser. Once the laser switches to the standby mode, the operator dials in the temperature at which the probe is to be maintained. The operator then sets the duration of the heating cycle either at a specified interval or for continuous operation by pressing the appropriate button on the front panel of the laser as previously explained in the '872 patent. While viewing the target blood vessel with an imaging system such as pulse radiography, the physician inserts the thermoangioplasty probe of the present invention within the blood vessel in close proximity to the obstruction. The operator then sets the laser to the treatment mode by pressing the appropriate button of the laser front panel illustrated in the '872 patent. While moving the probe either in an antigrade or retrograde fashion across the obstruction, the operator activates probe heating by pressing the laser foot switch illustrated an described in the '872 patent and also referred to in FIGS. 18 and 20 of the present invention. Laser power is automatically and continuously adjusted to achieve and maintain the tip temperature at the preset level. The actual amount of power delivered at any instant will be dependent on the preset temperature, the size of the probe tip and the dynamic environment encompassing the probe tip.

With specific reference to FIG. 18, ramp generator 182 acts to prevent an extremely sharp increase in probe temperature which could occur with the smaller diameter probes. A speed up circuit 184 accelerates the increase in the laser power for the larger diameter probes. A balance of these two components insures a quick response of the lasing system to temperature differentials with a minimum of temperature overshoot generally in the range of being less than 10% for temperatures from 50° to 450° Celsius. The surface temperature for probes with tip diameters of 3.0 millimeters or less reach the preset temperature established by dialing the temperature set 180 illustrated in FIG. 18 in under a second while probes with tip diameters of 3.5 to 4.0 millimeters reach preset temperature in under 3 seconds.

With continuing reference to FIG. 18 the voltage from the thermocouple T is coupled to a surge protection circuit 186 which prevents damage to the control network in the event of a high surge of voltages emanating from the use of a defibrillator on the patient during the angioplasty procedure. The input voltage is amplified by a low noise differential input amplifier 188. Electrical isolation from the laser or "earth ground" is achieved by use of an isolated power supply 190 and isolation amplifier 192. The output of the isolation amplifier 192 is used as one input to a temperature error detector 194.

The second input to the error detector 194 is generated by summing the output of the front panel mounted temperature selection potentiometer, i.e. the temperature set 180 illustrated in FIG. 18, and the ramp generator 182. The addition of the signal from the ramp generator 182 to the set point voltage generated by the temperature set 180 provides a controlled rate of increase of the temperature of the probe tip 22 (FIG. 1). The previously referred to speed up circuit 184 is placed in parallel with the error detector 194 to provide a faster rate of temperature increase for larger error conditions which improves the response time of the large size probe tips.

The output of temperature detector 194 is coupled to one input of the laser power error detector 200. The second input to the laser power error detector 200 comprises a light feedback signal generated by photo detector 202 and amplified by amplifier 204. Photo detector 202 detects the level of light entering the optical fiber 18. Photo detector 202 compares to light detector 65 shown in FIG. 2 of the '872 patent. The output of the laser power error detector 200 is in turn connected to the laser power control as generally indicated in FIG. 18.

The temperature control system of the invention also includes, as illustrated in FIGS. 18 and 20, a protection against open and shorted thermocouple wires. The open circuit condition is indicated if the thermocouple impedance is above a selected value. The short circuit condition is indicated if the temperature has not increased past a selected value in a specified time after the start of the treat cycle. This temperature protection circuitry is generally illustrated in FIG. 18 and in more detail in later described FIG. 20.

With specific reference to FIG. 18, a shorted thermocouple detector 206 is connected to flip flop 208 and an open thermocouple detector 210 is connected to a separate flip flop 212. The output of flip flops 208, 212 are in turn connected to a NOR gate 214 which in turn is connected to the fault output/standby reset circuitry of the laser system. As also indicated in FIG. 18 the clock input of flip flop 212 is fed through a timer 216 from the cycle start/foot switch down control of the laser with which the present invention is incorporated.

Either a thermocouple short or thermocouple open error condition will set the corresponding flip flop 208 or 212 which in turn will reset the laser to the standby condition as indicated in FIG. 18. The flip flops 208 and 212 are reset by the front panel "standby" switch as indicated by the circuit connection 220 to the reset/standby select switch illustrated in FIG. 18.

A somewhat more detailed thermocouple short and open detection circuitry is illustrated in FIG. 20 in which the output of the thermocouple amplifying circuitry is shown in FIG. 20 being fed on line 230 of FIG. 20 to the open circuit comparator 210 in which the thermocouple amplifier output is compared to a voltage equal to a thermocouple temperature of 800° C. The input amplifier 188 indicated in FIG. 18 includes a high resistance path from the thermocouple input to the positive supply voltage. Thus, an open circuit condition will result in an apparent thermocouple temperature in excess of 800° C.

The short circuit comparator 206 uses a reference that is proportional to a thermocouple temperature of 43° C. The output of the two comparators 206, 210 shown in FIG. 20 are coupled to the respective flip flops 208 and 212. For the open circuit condition the comparator output will set flip flop 212 the output of which is coupled via the NOR gate 214 to the fault output/standby reset circuitry of the laser. The output from the short circuit comparator 206 is connected to flip flop 208. Timer 216 is started when the foot switch is depressed and times out in 250 milliseconds. The timer output is coupled to the clock output in flip flop 208 and sets flip flop 208 if the input thermocouple amplifier output has not exceeded a value proportional to a temperature of 25° C. in the 250 milliseconds. The output of flip flop 208 is also coupled to the fault output/standby reset circuitry of the laser via the NOR gate 214. As previously indicated both flip flop 208 and flip flop 212 are reset by the laser standby switch located on the front panel of the laser. The mentioned times and temperatures are, of course, given by way of example and may vary as required for a particular procedure.

Aspects of the invention circuitry previously described in reference to FIGS. 18 and 20 may be viewed in a more general conceptual sense by reference to FIG. 19. In FIG. 19 the indicated voltage A proportional to measured temperature represents a voltage developed by the thermocouple T of FIG. 18. The voltage B of FIG. 19 represents the voltage established by the temperature set 180 of FIG. 18 to produce a voltage proportional to the desired temperature. The voltage C of FIG. 19 represents a voltage generated by the light feedback signal generated by the photo detector 202 of FIG. 18. As further indicated in FIG. 19 voltages A, B and C are received by the circuitry of FIG. 18 and are compared and processed to develop a control signal S for controlling the laser power source according to the equation $(A-B)-C=S$, the desired control signal.

In operation, the distal end of the laser angioplasty probe incorporating the thermocouple sensor of the invention may be inserted into a guide catheter of a type which is conventionally employed and readily commercially available in a multitude of sizes and configurations. The probe, which by virtue of the short length of the probe assembly and its optical fiber and thermocouple connection is highly flexible in character, facilitating guideability of the device, is threaded through the guide catheter. The probe tip with its thermocouple sensor thus is guided to the tissue treatment site and positioned in contact with the blood vessel blockage. As previously indicated, x-ray visualization techniques can be employed to facilitate precise positioning of the tip when the probe assembly is constructed of a radiopaque material. The precise positioning of the probe assembly tip is further enhanced by the flexibility of the optical fiber and thermocouple leads which as indicated may allow for insertion of the probe into the target blood vessel without the assistance of a guide catheter, particularly in the case of smaller diameter probe assemblies.

The proximal end of the optical fiber and thermocouple leads of the angioplasty device are attached, respectively, to a suitable source of laser energy and control circuitry, for transmission and control of such energy through the optical fiber to the probe assembly. The beam emerging from the laser is focused into the proximal end of the optical fiber, and the laser energy emerging at the distal end of the fiber is absorbed either by the tip itself, or by a high emissivity core of material in thermal contact with the tip, as shown in FIG. 6 and the temperature is detected by the thermocouple elements of the invention. Regardless of whether the laser energy is transmitted directly, or indirectly (i.e., via conversion to thermal energy in a high emissivity core) to the probe assembly tip, the heat resulting from the conversion of such laser energy is conducted by the tip to its outer surface, for the production of rapid and intense localized heating.

As a result, intravascular plaque and/or thrombi in contact with, or in close proximity to, the probe assembly tip, are subjected to such intense heating. The thermal conductivity of the probe assembly, and the curvoidal shape of its tip, facilitate a rapid uniform transfer of heat during laser activation, and provide a comparable rapid dissipation of heat and equilibration of tip temperature with intravascular temperature during cooling, i.e., laser deactivation. Simultaneously, the tip temperature is both measured and controlled by the unique thermocouple sensing and control system of the invention.

During laser activation, heat traversing the tip of the probe assembly is also conducted proximally toward the optical fiber. The construction of the present invention avoids damage to the optical fiber and ensures the mechanical integrity of the probe assembly's connection to the optical fiber while maintaining a short overall tip and probe assembly length, by the provision of an extended heat dissipation path in the helically wound conductive wire coil serving as a means for connecting the probe body to the optical fiber.

In summary, at least these advantages are achieved:
(a) Temperature control of the probe is directly coupled to the laser light feedback system.
(b) Temperature response of the probe is maximized with little or no overshoot of the preset temperature.
(c) A balance between ramping and speed-up components allows the circuit to handle probes significantly different in size, mass and volume without having to set the control circuit according to the size probe utilized.
(d) Incorporation of safeguards for protection of both patient and circuit is achieved.
(e) Rapid temperature response time is achieved for probes of different size.
(f) Probe temperature is maintained within plus or minus ten percent (10%) of preset temperature in both stagnant and flowing fields.
(g) Blood flow changes are met with millisecond response times.
(h) A single composite cable incorporates both the optical fiber for transferring laser energy from the laser source to the treatment site and thermocouple leads for transferring the sensed temperature signal from the treatment site to the control for the laser source.
(i) Temperature control is achieved substantially independent of laser tube life and condition.
(j) Does not require a calibration relating laser tube current to laser output power as with an alternative form of control.

Although specific features and embodiments of the invention have been described in detail, it will be appreciated that other embodiments, modifications, and variations are possible, and accordingly all such embodiments, modifications and variations are to be regarded as being within the spirit and scope of the present invention.

What is claimed is:
1. A laser-energizable thermal probe system, comprising:

(a) a microsize optical fiber having a proximal end portion connectable to a laser energy source for transmission of laser energy therethrough to a distal end portion thereof;

(b) a laser energy source connected to said proximal end portion of said optical fiber including means for controlling the level of laser energy produced thereby;

(c) a probe assembly connected to said distal end portion of said fiber, comprising:

(i) a thermally conductive probe body including a curvoidal tip and a neck portion joined to said tip and extending proximally therefrom, with an interior passage in said probe body extending between proximal and distal portions of the passage through said neck portion and containing the said distal end portion of said optical fiber whereby laser energy produced by said source and transmitted by said optical fiber to said probe body and converted to thermal energy is transmittable by said tip to a selected site in contact with said tip;

(ii) thermally conductive means mounted to join said optical fiber to said probe body and to provide an extended heat transfer dissipation path for heat generated by said probe assembly in use; and (iii) a thermocouple assembly including a thermocouple secured proximate and in operative thermal association with the outer surface of said probe body to sense the outer surface temperature thereof and positioned so as to avoid impingement of laser energy thereon and a pair of microsize thermocouple leads with distal and proximal ends extending from said thermocouple;

(d) said optical fiber and thermocouple leads being formed as an integral composite optical fiber-thermocouple lead flexible cable suited to transmitting heat producing radiation to said selected site in a human body cavity as in an arterial or venous channel into which the cable is fed and when necessary bending to accommodate to the curvature of the channel without directional preference and transmitting from the same selected site through said leads signals indicative of the outer surface temperature of said probe body;

(e) control means for said laser energy source connected to said thermocouple leads and rapidly responsive to an output signal developed by the thermal condition of said thermocouple to maintain and rapidly regulate said laser energy source at some level of power and regulate such level corresponding to a predetermined temperature of the outer surface of and size of said probe body; and (f) matable coupling means joined to said optical fiber and leads at a respective proximal portion and proximal end thereof for connecting said optical fiber to said laser energy source and said thermocouple leads to said control means.

2. A system as claimed in claim 1 wherein said thermally conductive means comprises a helically wound thermally conductive wire having distal and proximal portions and joined at its distal portion to said probe body neck portion and at its proximal portion to said optical fiber.

3. A system according to claim 2, wherein said helically wound conductive wire is formed of a metal selected from the group consisting of platinum, irridium, and alloys thereof.

4. A system as claimed in claim 1 including a discrete mass of a laser energy absorptive, high emissivity medium interiorly contained in a distal portion of said passage within said curvoidal tip with the distal end portion of said optical fiber having a polished face located in intimate contact with said mass.

5. A system as claimed in claim 1 wherein said thermally conductive means forms a cavity and including a heat resistant composition filling said cavity and passage to substantially eliminate forming of gas therein.

6. A system as claimed in claim 1, wherein said probe body is formed of a metal selected from the group consisting of platinum, irridium, and alloys thereof.

7. A system as claimed in claim 1 wherein said control means includes means responsive to open and short circuit conditions in said leads to reset the laser energy source to a standby condition.

8. A laser system for transmitting light through an optical fiber, comprising:

(a) a microsize optical fiber having proximal and distal end portions;

(b) a laser energy source connected to the proximal end portion of said optical fiber including means for controlling the level of laser energy produced thereby;

(c) a heat generating element secured to the distal end portion of said fiber;

(d) a thermocouple assembly including a thermocouple secured proximate and in operative thermal association with the outer surface of said heat generating element and made up of thermocouple wires of dissimilar metal with proximal and distal ends and microsize leads extending therefrom, said optical fiber and leads being encased together to form an integral flexible cable extending between said heat generating element and laser energy source and of a size suited to being fed into arterial and venous channels; and (e) a monitoring circuit connected through said leads to proximal ends of said thermocouple wires and including means to develop a signal voltage proportional to a desired outer surface temperature of said heat generating element, a signal voltage proportional to the outer surface temperature of said heat generating element as measured by said thermocouple and a signal voltage proportional to the level of light entering the proximal end portion of said fiber and means for comparing and processing said signal voltages to develop a control signal for adjusting the output of said laser energy source to produce a temperature on the outer surface of said heat generating element corresponding to said desired temperature.

9. In a laser system as claimed in claim 8 wherein said monitoring circuit includes means responsive to open and short circuit conditions in said leads to reset the laser energy source to a standby condition.

10. A laser energizable thermal probe system, comprising:

(a) a composite optical fiber-thermocouple lead element having a lengthwise extending microsize optical fiber and pair of microsize thermocouple leads encased together within a surrounding jacket, said element having proximal and distal end portions and being sufficiently flexible and of a size suited to being fed into arterial and venous channels;

(b) a laser energy source connected to the proximal end portion of said optical fiber for transmission of laser energy therethrough to a distal end portion thereof including means for controlling the level of laser energy produced thereby;

(c) a thermally conductive probe body joined to the distal end portion of said optical fiber whereby laser energy produced by said source and transmitted by said optical fiber to said probe body and converted to thermal energy is transmittable by said probe body to a selected site in contact with said probe body;

(d) a thermocouple joined to distal ends of said leads and secured to and in operative thermal association with the outer surface of said probe body to sense the outer surface temperature thereof; and (e) a monitoring circuit connected to proximal ends of said thermocouple leads and including means to develop a signal voltage proportional to a desired outer surface temperature of said probe body, a signal voltage proportional to the temperature measured by said thermocouple and a signal voltage proportional to the level of light entering the proximal end portion of said fiber and means for comparing and processing said signal voltages to develop a control signal for adjusting the output of said laser energy course to produce a temperature on the outer surface of said probe body corresponding to said desired temperature.

11. In a probe system as claimed in claim 10 wherein said monitoring circuit includes means responsive to open and short circuit conditions of said leads to reset the laser energy source to a standby condition.

12. A laser system for transmitting light through an optical fiber, comprising:
(a) a microsize optical fiber having proximal and distal end portions;
(b) a laser energy source connected to the proximal end portion of said optical fiber including means for controlling the level of laser energy produced thereby;
(c) a heat generating element secured to the distal end portion of said fiber;
(d) a thermocouple assembly including a thermocouple secured proximate and in operative thermal association with the outer surface of said heat generating element and made up of thermocouple wires of dissimilar metal and microsize leads extending therefrom, said optical fiber and leads being encased together to form an integral flexible cable extending between said heat generating element and laser energy source, said cable being sufficiently flexible and of a size suited to being fed into arterial and venous channels; and
(e) control means for said laser energy source connected to said thermocouple leads and rapidly responsive to an output signal developed by the thermal condition of said thermocouple to maintain and rapidly regulate said laser energy source at some level of power and regulate such level corresponding to a predetermined outer surface temperature of said heat generating element generated in the vicinity of said thermocouple and the size of said heat generating element.

13. A laser-energizable medical treating system, comprising:
(a) a laser energy source including means for controlling the level of laser energy produced thereby;
(b) a composite optical fiber-thermocouple lead element extending between distal and proximal ends and having a distally mounted heatable probe of approximately four millimeters in diameter or less and connected to said laser source and comprising:
(i) a lengthwise extending optical fiber of substantially 600 micron diameter or less;
(ii) a pair of parallel non-overlapping thermocouple leads each of substantially less size than the size of the fiber and extending for the length of said fiber, the distal ends of said leads being connected to the outer surface of said probe; and
(iii) a casing surrounding said optical fiber and leads and of less than four millimeters in overall diameter; and
(c) said optical fiber, thermocouple leads and casing forming said element as a flexible cable suited to transmitting heat producing radiation to a selected site in a human body cavity as in an arterial or venous channel into which the cable including said probe is fed and when necessary bending to accommodate to the curvature of the channel without directional preference and transmitting from the same selected site through said leads signals indicative of the outer surface temperature of said probe.

14. A laser-energizable thermal probe medical treating system, comprising:
(a) a microsize optical fiber having proximal and distal end portions;
(b) a laser energy source connected to the proximal end portion of said optical fiber including means to control the level of laser energy produced thereby;
(c) a heat generating element secured to the distal end portion of said fiber and formed for passage into a selected human body opening of comparable size such as a venous or arterial channel;
(d) temperature sensing means in operative thermal association with the outer surface of said heat generating element for sensing the temperature of said outer surface and having a pair of microsize electrical leads extending therefrom for the length of said fiber, said optical fiber of one size and leads of substantially lesser size being encased together in a microsize casing to form a flexible cable capable of passing through said opening, and extending between said heat generating element and laser energy source; and
(e) control means for said laser energy source connected to said leads and responsive to an output condition developed by the thermal condition of said temperature sensing means to maintain said laser energy source at some level of power corresponding to a predetermined outer surface temperature of said heat generating element.

15. A laser-energizable thermal heating system, comprising:
(a) a microsize optical fiber having proximal and distal end portions;
(b) a laser energy source connected to the proximal end portion of said optical fiber including means for controlling the level of laser energy produced thereby;
(c) a heat generating element formed of highly thermally conductive material and secured to the distal end portion of said fiber by highly thermally conductive means providing an extended rapid heat transfer dissipation path for heat generated by said heat generating element in use;
(d) rapidly responsive temperature sensing means in operative thermal association with the outer surface of said heat generating element for rapidly sensing the temperature of said outer surface and having a pair of electrical leads extending therefrom for the length of said fiber, said optical fiber of one size and leads of substantially lesser size being encased together in a casing for a major portion of the length thereof and forming a flexible cable extending between said heat generating element and laser energy source and suited to being fed with said heat generating element into a venous or arterial channel; and (e) control means for said laser energy source connected to said leads and rapidly responsive to an output condition developed by the thermal condition of said temperature sensing means to maintain and rapidly adjust said laser energy source when required at some level of power corresponding to a predetermined outer surface temperature of said heat generating element.

16. A laser energizable thermal system as claimed in claim 15 wherein said control means includes means rapidly responsive to open and short circuit conditions in said leads to reset the laser energy source to a standby condition.

17. A laser energizable thermal system as claimed in claim 15 wherein said control means includes means rapidly regulating the rate of adjusting said laser energy source thereby enabling said control means to accommodate to different sizes of said heat generating element.

18. A laser energizable thermal system as claimed in claim 17 wherein said control means includes means rapidly responsive to open and short circuit conditions in said leads to reset the laser energy source to a standby condition.

* * * * *

UNITED STATES PATENT AND TRADEMARK OFFICE
CERTIFICATE OF CORRECTION

PATENT NO.  : 4,899,741

DATED       : February 13, 1990

INVENTOR(S) : Joseph R. Bentley, Radford G. Ferre, Steven W. Kovalcheck

It is certified that error appears in the above-identified patent and that said Letters Patent is hereby corrected as shown below:

Column 1, line 9, correct "4,760,209" to read --4,760,845--.

Column 5, line 59, correct "003,20" to read --003,209--.

Column 9, line 41, correct "sows" to read --shows--.   (PTO

Signed and Sealed this

Fifth Day of February, 1991

Attest:

HARRY F. MANBECK, JR.

*Attesting Officer*      Commissioner of Patents and Trademarks